United States Patent
Cotton

(10) Patent No.: US 12,127,913 B2
(45) Date of Patent: Oct. 29, 2024

(54) ABSORBENT WOUND DRESSINGS

(71) Applicant: BRIGHTWAKE LIMITED, Nottingham (GB)

(72) Inventor: Stephen Cotton, Nottingham (GB)

(73) Assignee: BRIGHTWAKE LIMITED, Nottingham (GB)

(*) Notice: Subject to any disclaimer, the term of this patent is extended or adjusted under 35 U.S.C. 154(b) by 0 days.

(21) Appl. No.: 17/553,061

(22) Filed: Dec. 16, 2021

(65) Prior Publication Data

US 2022/0142822 A1    May 12, 2022

Related U.S. Application Data

(63) Continuation of application No. 14/783,385, filed as application No. PCT/GB2014/051086 on Apr. 8, 2014, now abandoned.

(30) Foreign Application Priority Data

Apr. 8, 2013    (GB) .................................... 1306317

(51) Int. Cl.
*A61F 13/02*    (2024.01)
*A61F 13/01*    (2024.01)
(Continued)

(52) U.S. Cl.
CPC .... *A61F 13/0209* (2013.01); *A61F 13/01012* (2024.01); *A61F 13/01017* (2024.01); *A61F 13/01029* (2024.01); *A61F 13/01042* (2024.01); *A61F 13/022* (2013.01); *A61F 13/0223* (2013.01); *A61F 13/0253* (2013.01);
(Continued)

(58) Field of Classification Search
CPC ............ A61F 13/0209; A61F 13/00012; A61F 13/00017; A61F 13/00029; A61F 13/00042; A61F 13/0223; A61F 13/0253; A61F 13/022; A61L 15/60; A61L 15/16; A61L 15/42
See application file for complete search history.

(56) References Cited

U.S. PATENT DOCUMENTS 3,580,801 A    5/1971    Spence
3,653,383 A    4/1972    Wise
(Continued)

FOREIGN PATENT DOCUMENTS

EP    0 280 253 A2    8/1990
GB    2401879 A    11/2004
(Continued)

OTHER PUBLICATIONS

Great Britain Search Report for related GB1306317.7, 3 pages (Sep. 24, 2013).
(Continued)

*Primary Examiner* — Camtu T Nguyen
(74) *Attorney, Agent, or Firm* — Troutman Pepper Hamilton Sanders LLP (Rochester)

(57) ABSTRACT

An absorbent wound dressing (1) comprising a superabsorbent material (13) that is in fluid communication with the surface of a wound to which the dressing is applied when in use. The superabsorbent material (13) is enclosed in an envelope (14,15) having a wound-facing surface that is knitted or woven from a yarn comprising gelling fibres.

22 Claims, 2 Drawing Sheets

(51) Int. Cl.
*A61F 13/0203* (2024.01)
*A61F 13/0206* (2024.01)
*A61F 13/0246* (2024.01)
*A61L 15/24* (2006.01)
*A61L 15/26* (2006.01)
*A61L 15/28* (2006.01)
*A61L 15/60* (2006.01)

(52) U.S. Cl.
CPC ............... *A61L 15/24* (2013.01); *A61L 15/26* (2013.01); *A61L 15/28* (2013.01); *A61L 15/60* (2013.01)

(56) References Cited

U.S. PATENT DOCUMENTS

| | | | |
|---|---|---|---|
| 4,643,180 A | 2/1987 | Feld et al. | |
| 4,948,575 A | 8/1990 | Cole et al. | |
| 5,017,625 A * | 5/1991 | Ansell | C08G 18/283 |
| | | | 528/49 |
| 5,482,932 A | 1/1996 | Thompson | |
| 5,718,916 A | 2/1998 | Scherr | |
| 5,792,089 A | 8/1998 | Penrose et al. | |
| 5,817,391 A | 10/1998 | Rock et al. | |
| 6,075,177 A | 6/2000 | Bahia et al. | |
| 6,268,544 B1 | 7/2001 | Court et al. | |
| 7,128,929 B1 | 10/2006 | Scherr | |
| 7,276,275 B2 | 10/2007 | Schindzielorz et al. | |
| 9,132,225 B2 | 9/2015 | Gourlay et al. | |
| 2004/0260225 A1 | 12/2004 | Bishop et al. | |
| 2005/0215932 A1 | 9/2005 | Sigurjonsson et al. | |
| 2005/0249791 A1 | 11/2005 | Hobbs et al. | |
| 2007/0255194 A1 | 11/2007 | Gundnason et al. | |
| 2008/0312572 A1 | 12/2008 | Riesinger | |
| 2009/0287130 A1 * | 11/2009 | Lee | A61F 13/36 |
| | | | 602/44 |
| 2010/0042034 A1 * | 2/2010 | Riesinger | A61L 15/60 |
| | | | 602/44 |
| 2010/0159192 A1 * | 6/2010 | Cotton | A61L 15/58 |
| | | | 428/137 |
| 2010/0185163 A1 | 7/2010 | Heagle | |
| 2011/0070391 A1 | 3/2011 | Cotton | |
| 2011/0125110 A1 | 5/2011 | Cotton | |
| 2011/0213286 A1 | 9/2011 | Riesinger | |
| 2011/0229688 A1 | 9/2011 | Cotton | |
| 2011/0272343 A1 | 11/2011 | Gourlay et al. | |
| 2011/0313383 A1 | 12/2011 | Hofstetter et al. | |
| 2012/0022479 A1 | 1/2012 | Cotton | |
| 2012/0034432 A1 | 2/2012 | Cotton | |
| 2012/0095419 A1 | 4/2012 | Riesinger | |
| 2012/0107375 A1 | 5/2012 | Cotton | |
| 2012/0116281 A1 | 5/2012 | Cotton | |
| 2012/0175319 A1 | 7/2012 | Cotton et al. | |
| 2012/0269879 A1 | 10/2012 | Watson | |
| 2013/0053748 A1 | 2/2013 | Cotton | |
| 2014/0309574 A1 * | 10/2014 | Cotton | A61L 15/225 |
| | | | 602/44 |
| 2016/0067107 A1 * | 3/2016 | Cotton | A61L 15/26 |
| | | | 602/44 |

FOREIGN PATENT DOCUMENTS

| | | | |
|---|---|---|---|
| GB | 2 496 310 A * | 11/2012 | |
| WO | 95/19795 A1 | 7/1995 | |
| WO | 98/09590 A1 | 3/1998 | |
| WO | 98/46818 A1 | 10/1998 | |
| WO | 99/64080 A1 | 12/1999 | |
| WO | 99/67456 | 12/1999 | |
| WO | 01/23653 A1 | 4/2001 | |
| WO | 2004/084961 A1 | 10/2004 | |
| WO | 2005/079718 A1 | 9/2005 | |
| WO | 2007/003905 A1 | 1/2007 | |
| WO | 2011/058311 A1 | 6/2011 | |
| WO | 2011/077096 A1 | 6/2011 | |

OTHER PUBLICATIONS

International Search Report and Written Opinion for corresponding PCT/GB2014/051086, 4 pages (mailed Jun. 2, 2014).

International Preliminary Report on Patentability for International Application No. PCT/GB2014/051086 (dated Oct. 13, 2015).

Mao et al., "Structure and Character of Artificial Muscle Model Constructed from Fibrous Hydrogel," Current Applied Physics 5:426-28 (2005).

Boateng et al., "Wound Healing Dressings and Drug Delivery Systems: A Review," Journal of Pharmaceutical Sciences 97(8):2892-2923 (2008).

3M Healthcare et al., "Wundheilung", http://www.wundheilung.neVProdukVAIginate.html (Dec. 4, 2010).

Khanlari et al., "Effect of pH on Poly(acrylic acid) Solution Polymerization", Journal of Macromolecular Science, Part A: Pure and Applied Chemistry, 52:587-592 (2015).

* cited by examiner

ABSORBENT WOUND DRESSINGS

This application is a continuation of U.S. patent application Ser. No. 14/783,385, which is a national stage application under 35 U.S.C. § 371 of PCT Application No. PCT/GB2014/051086, filed Apr. 8, 2014, which claims the priority benefit of Great Britain Application No. 1306317.7, filed Apr. 8, 2013.

FIELD OF THE INVENTION

The present invention relates to absorbent wound dressings.

BACKGROUND OF THE INVENTION

Different types of wound dressing are required to meet different clinical needs. However, a common requirement for wound dressings is that they should be able to absorb exudate from a wound, while retaining sufficient structure that they can be easily removed from the wound after use. If a wound dressing cannot be cleanly removed from a wound then a patient will suffer additional trauma. In addition, if fragments of the dressing may be left in the wound, healing may be inhibited.

In addition to the need to retain structural integrity, it is important for many applications that a wound dressing is able to absorb a significant amount of liquid. During the healing process, wounds produce exudate. This is absorbed by the dressing in order to keep the wound clean and promote healing. A determining factor in how regularly a dressing needs to be changed is how quickly the dressing becomes saturated with exudate. Infrequent dressing changes are preferable as changing a dressing can aggravate a wound, as well as causing pain and/or discomfort for the patient.

Gelling fibres such as alginate or pectin fibres are known for use in wound dressings. They have a greater capacity for absorbing liquid than standard textile fibres and, on absorbing liquid, they become moist and slippery. This prevents the dressing from adhering to the wound and therefore makes removal of the dressing easier. However, it also causes the gelling fibres to lose structural integrity, making them more difficult to handle, and more difficult to remove cleanly from a wound. In addition, the gelling fibres themselves may be brittle, making them difficult to work with in the production of wound dressings. Hence, despite their advantages, gelling fibres have generally been used in wound dressings only in the form of non-woven fabric. However, non-woven fabrics generally have a low tensile strength, resulting in a loss of integrity when the dressing is saturated with liquid. In addition, non-woven fabrics may shed fibres, a trait which is extremely undesirable in a wound dressing.

Superabsorbent materials have also been used in wound dressings, particularly in dressings for wounds that produce very high levels of exudate.

However, superabsorbent materials are often produced as free flowing powders and a problem associated with this when such materials are used in wound dressings is that the powder can easily transfer into the wound from the dressing. If particles of superabsorbent materials are left in the wound, wound healing can be inhibited. For some wounds in particular, for example sinus wounds, it is essential that all of the material is removed when the wound dressing is changed, as cases of giant cell foreign body reaction have been reported.

It is therefore important that superabsorbent material be kept away from the wound surface whilst still allowing wound exudate to reach the superabsorbent material. It is also important that the means used to contain the superabsorbent material is not adherent to the wound surface.

DESCRIPTION OF THE INVENTION

Figure 1:
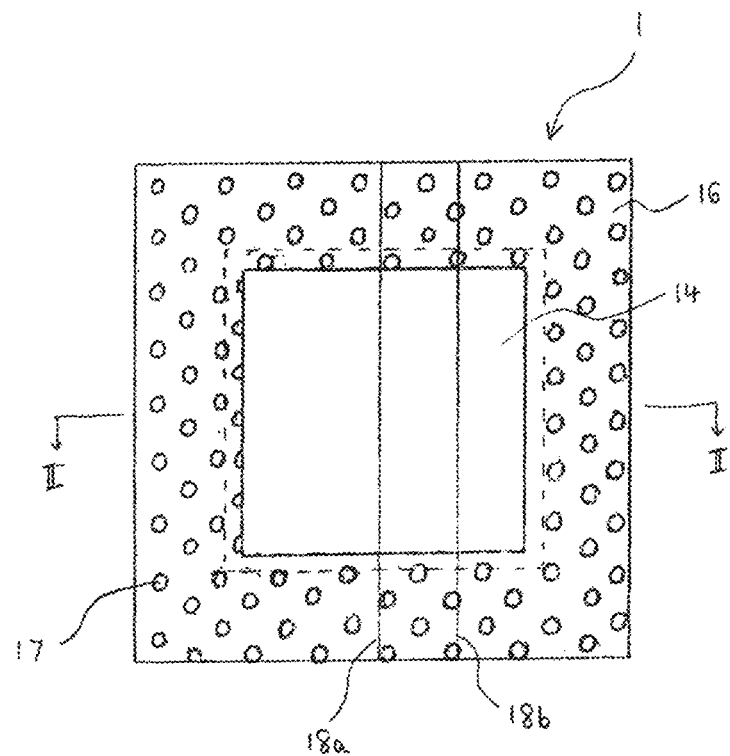
FIG. 1 shows an underside plan view of a first embodiment of a wound dressing according to the invention.

There has now been devised an improved form of wound dressing comprising superabsorbent material, which has a non-adherent wound-facing surface that allows exudate to reach the superabsorbent material whilst preventing the superabsorbent material from reaching the wound.

According to the invention there is provided an absorbent wound dressing comprising a superabsorbent material that, in use, is in fluid communication with the surface of a wound to which the dressing is applied, wherein the superabsorbent material is enclosed in an envelope having a wound-facing surface knitted or woven from a yarn comprising gelling fibres.

The dressing according to the invention is advantageous primarily in that because the superabsorbent material is contained within the envelope, the risk of particles of superabsorbent material entering the wound is substantially reduced. The wound-facing surface of the envelope nonetheless permits wound exudate to flow into the envelope, and because that surface comprises gelling fibres, it gels in use and hence becomes non-adherent, thereby facilitating removal of the dressing from the wound without causing trauma to the wound or pain to the patient.

In the wound dressing of the invention, the superabsorbent material is contained within an envelope. The envelope typically comprises two sheets of material that are joined around their edges to encapsulate the superabsorbent material between them. The first, wound-facing sheet is generally a sheet of material knitted or woven from a yarn comprising gelling fibres. The second, reverse sheet may be of similar material, but generally does not need to be and usually will not be.

In some embodiments of the invention, the reverse sheet of the envelope is a sheet of any suitable material, most commonly a sheet of synthetic plastics material, such as a polyester film or web. In general, any material that can be bonded to the wound-facing sheet and which is suitably impervious to the superabsorbent material may be used. In such embodiments, the envelope may be assembled from the two sheets of material, with the superabsorbent material between them, and the assembled envelope incorporated into the dressing as a whole. Producing the envelope separately provides advantages in that the superabsorbent material is enclosed prior to the final construction of the dressing. This lessens the likelihood of loose superabsorbent material being unintentionally present in any part of the dressing other than the envelope. The envelope can be formed by joining the knitted or woven fabric and the second piece of material together at their edges. This can be done by any suitable means known in the art but preferably by welding. Preferably the welding is performed using heat. Most preferably it is performed using heated platens.

The entire envelope can be affixed to an adjacent component of the dressing, for instance the backing layer that commonly forms a component of such dressings, by any suitable means, preferably using an adhesive or by welding. If an adhesive is used, the adhesive is preferably an acrylic adhesive.

In other embodiments of the invention, the reverse sheet of the envelope is the backing layer itself, ie the superabsorbent material is contained within an envelope constructed from a sheet of fabric knitted or woven from yarn comprising gelling fibres that is affixed to a backing layer. Generally, the backing layer will be of greater dimensions than the sheet of knitted or woven fabric, such that the backing layer extends beyond the knitted or woven fabric sheet and provides a means of affixing the wound dressing to the skin.

The knitted or woven material that forms the wound-facing surface of the envelope has an open structure that allows exudate from a wound to pass through it as well as be absorbed by it.

By "gelling fibre" is meant in relation to the invention fibres that are capable of absorbing aqueous fluid, such as wound exudate, and which on absorbing liquid become gel-like, moist and slippery. The gelling fibres may have an absorbency of at least 2 grams 0.9% saline solution per gram of fibre, as measured by the free swell absorbency test (ie dispersing a known dry weight of fibre in the test liquid (saline) for sufficient time for the fibre to absorb liquid, removing the excess liquid by vacuum filtration, and measuring the increase in weight of the fibre). The absorbency may be considerably higher, eg at least 5 g/g, or at least 10 g/g, or at least 15 g/g, or at least 25 g/g.

The gelling fibres may be any suitable gelling fibre known in the art, including pectin fibres, alginate fibres, fibres made from alginate and another polysaccharide, chitosan fibres, hyaluronic acid fibres, fibres of other polysaccharides or derived from gums, or chemically-modified cellulosic fibres, eg carboxymethyl cellulose (CMC). The gelling fibres may be a combination or blend of different gelling fibres.

Currently preferred gelling fibres are alginate fibres and pectin fibres.

Alginates are high molecular weight, hydrophilic polymers, which are derived from seaweed and which form a gel on contact with aqueous fluids. Their hydrophilic nature encourages the absorption of liquid such as wound exudate, making them extremely useful in wound dressings.

The alginate polymer is formed of two basic monomeric units, mannuronic acid and guluronic acid. Differing proportions of these units in the polymer alter the properties of the alginate. In addition to this, alginate polymers are associated with cations, and are normally produced in the form of sodium alginate, calcium alginate or a sodium/calcium alginate mix. Other forms, such as potassium alginate, are also known.

The nature of the cation which is associated with the alginate polymer changes the properties of the alginate. For example, sodium alginate is water soluble, whereas calcium alginate is not. By altering the alginate used in a wound dressing it is therefore possible to ensure that the final dressing displays the desired characteristics.

Pectins are a family of complex polysaccharides comprising 1,4-linked γ-D-galactosyluronic residues, found primarily in the cell walls of terrestrial plants. Pectins can be separated into two main groups which have different gelling properties: low-methoxy and high-methoxy pectins. Low-methoxy pectins are pectins in which less than half the carbonyl groups in the chain of galacturonic residues are esterified with methanol. Low-methoxy pectins can form a gel in the presence of divalent cations (eg calcium), due to non-covalent ionic interactions between blocks of galacturonic acid residues and the divalent ion. High-methoxy pectins are those in which more than half of the carbonyl groups have been esterified with methanol. Such pectins can gel in the presence of sugar and acid, forming two-dimensional networks of pectin molecules in which the solvent (water) is immobilised with the sugar and acid co-solutes.

Another class of gelling fibres that are known to be useful in absorbent wound dressings are those made from chemically-modified cellulose. In particular, carboxymethylated cellulose fibres may be used, eg in the form of sodium carboxymethyl cellulose. Such fibres preferably have a degree of substitution of at least 0.2 carboxymethyl groups per glucose unit, or at least 0.3 or at least 0.5.

Methods for producing gelling fibres are known in the art, and any suitable method may be employed to produce fibres for use in the present invention. For example, calcium alginate fibres may be produced by solvent-spinning a sodium alginate solution through a solution of calcium ions. Similarly, pectin fibres may be produced by solvent-spinning a solution of the pectin polymer into a bath of a water-miscible organic solvent. The fibres may be further processed by any suitable method known in the art, including washing, crimping, carding, spinning and/or cutting.

The yarn from which the fabric is knitted or woven may comprise only gelling fibres. However, it is preferred that the yarn comprises a blend of gelling fibres and non-gelling fibres. Preferably the yarn comprises at least 50% w/w gelling fibres. The combination of gelling fibre and non-gelling fibre in a blended yarn produces a strong, flexible yarn that can be knitted or woven, despite the relatively low proportion of non-gelling fibre.

The knitted or woven structure comprising a blended yarn retains its structural integrity after use in the wound dressing. Even when saturated with liquid, the structure retains sufficient integrity that it can be easily removed from the wound with little or no breakage or disintegration.

Methods for producing yarn from blended fibres are known in the art, and the yarn used in the present invention may be made by blending gelling fibres and non-gelling fibres by any suitable method. Commonly, short lengths of fibre (staple fibres) are blended together before being spun into a yarn. Preferably, the staple fibres used in production of the yarn have a length greater than 30 mm. More preferably, they have a length greater than 40 mm. The length of the staple fibres may be less than 100 mm, eg 30-100 mm or 40-100 mm. The lengths of the staple fibres may be variable, in which case the mean length may be in the ranges specified above.

The non-gelling fibres may be any suitable fibres known in the art, or may be a mixture of two or more non-gelling fibres. The non-gelling fibres may be textile fibres, and may be natural, eg cotton, may be natural fibres which have been modified eg cellulosic fibres such as viscose or lyocell (sold under the trade name TENCEL®, or they may be synthetic, eg polyester, polypropylene or polyamide. Different fibres have different characteristics in terms of tensile strength and absorbency, and appropriate non-gelling fibres may be chosen according to the desired characteristics of the wound dressing. In addition, a combination of two or more non-gelling fibres may be used in order to achieve the desired characteristics. Preferably, the non-gelling fibres are natural fibres which have been modified. More preferably, the non-gelling fibres are cellulosic fibres.

Thus, in some embodiments of the invention, the yarn may comprise a combination of alginate fibres and cellulosic fibres. In such cases, the yarn preferably comprises a combination of calcium alginate fibres and cellulosic fibres. More preferably, the yarn comprises calcium alginate and viscose, or calcium alginate and lyocell.

In other embodiments of the invention, the yarn may comprise a combination of pectin fibres and cellulosic fibres. In such cases, the yarn preferably comprises a combination of pectin fibres and viscose, or pectin fibres and lyocell.

The ratio of gelling fibre to non-gelling fibre in the yarn can vary between quite wide limits, provided that the proportion of gelling fibre (by weight) in the blend is at least 50%. Preferably, the gelling fibre comprises 50-98% w/w of the blend. The gelling fibre may comprise 60-98% w/w of the blend, or 70-98% w/w of the blend. Preferably, the non-gelling fibre comprises 2-49% w/w of the blend. The non-gelling fibre may comprise 5-49% w/w of the blend, or 10-30% of the blend. Thus, the ratio of gelling fibre to non-gelling fibre may be from 98:2 to 51:49. The ratio of gelling fibre to non-gelling fibre may be from 98:2 to 60:40, more preferably from 98:2 to 70:30. For example, the ratio of gelling fibre to non-gelling fibre may be approximately 60:40, 65:35, 70:30, 75:25, 80:20, 85:15, 90:10, 95:5 or 98:2.

The proportions and ratios set out in the preceding paragraph may in general apply to any combinations of gelling and non-gelling fibres, eg combinations in which the gelling fibres are alginate fibres, pectin fibres or modified cellulose fibres, and combinations in which the non-gelling fibres are natural, eg cotton, natural fibres which have been modified eg cellulosic fibres such as viscose or lyocell, or synthetic fibres, eg polyester, polypropylene or polyamide. The same is true of the staple fibre lengths and absorbencies described above.

Methods for producing yarn from blended fibres are known in the art, and the yarn according to the present invention may be made by blending the gelling fibres and non-gelling fibres by any suitable method.

Most preferably, the fabric is knitted. Knitting is a process whereby fabric is formed by the interlocking of loops of yarn. A variety of knitting techniques are known in the art, and are suitable for use in the present invention.

Preferably, the structure is knitted using a double needle-bed. A double needle-bed produces a knitted fabric which has higher strength, and greater bulk, than knitted fabrics produced by other methods. This ensures that the structure has high structural integrity, and aids in the retention of integrity even after use.

Knitted fabrics may warp-knitted or weft-knitted. In warp-knitted fabrics, rows of loops are made along the length of the fabric (the warp). A common way to achieve this is to feed numerous lengths of yarn simultaneously to rows of individual needles. In weft-knitted fabrics, the loops are made horizontally across the fabric (the weft), normally using a single yarn, and the stitches are formed by the interlocking of the loops with loops of the rows above and below. Preferably, knitted structures according to the present invention are warp-knitted.

The yarn may be of any suitable type known in the art. In particular, the yarn may be a textured yarn, eg an air-intermingled yarn, false twist yarn, multiple-ply yarn, KDK (knit-deknit) yarn or other similar yarn.

In alternative embodiments of the invention, the fabric that forms the wound-facing surface of the envelope may be knitted or woven using yarns made entirely from gelling fibres and separate yarns of non-gelling fibres to provide reinforcement and greater strength to the fabric.

"Superabsorbent material" in the context of the present invention means a material that is capable of absorbing many times its own mass of water (eg up to 200, 300, 400, 500 or more times its own mass of water).

Although it should be appreciated that the wound dressing of the present invention may comprise any superabsorbent material, preferred superabsorbent materials are polymeric superabsorbent materials and include alginate, polyacrylate (ie a salt of polyacrylic acid), polyacrylamide copolymers, ethylene maleic anhydride copolymer, carboxymethylcellulose, polyvinylalcohol copolymers, polyethylene oxide and starch-grafted copolymers of polyacrylonitrile.

Many such superabsorbent materials may be used in particulate form. In such cases, the particles may be incorporated into a carrier material, for instance by being encapsulated between two layers of carrier material, eg tissue paper or the like.

Alginate superabsorbent may be sodium or calcium alginate. The alginate superabsorbent is preferably in the form of a non-woven mat, providing a superabsorbent layer suitable for the method of the present invention.

The most preferred superabsorbent material is sodium polyacrylate polymer. Sodium polyacrylate polymer is a solid crystalline material, and is preferably incorporated into a layer in the form of particles encapsulated between two layers of carrier material, such as tissue paper. A specific example of a suitable material is Gelok® 14040S/S manufactured by Gelok International Corporation.

The wound dressings according to the invention typically comprise a backing layer, which forms a barrier between the wound and the surrounding atmosphere. Any suitable material known in the art may be used for the backing layer.

The backing layer will generally be impermeable to wound exudate and other liquids, but is preferably permeable to air and moisture vapour. In particular, the backing layer preferably exhibits a relatively high moisture vapour transmission rate (MVTR). The MVTR of the backing layer may be at least 300 g/m$^2$/24 h, more suitably at least 500 g/m$^2$/24 h and preferably at least 700 g/m$^2$/24 h at 37° C. and 100% to 10% relative humidity difference.

The backing layer is most preferably a plastics film having the desired characteristics. The backing layer may be a polyurethane film.

The backing layer may be larger in size than the envelope, such that it extends beyond the edge of the envelope on one or more sides. Preferably, the backing layer extends beyond the edge of the envelope on all sides, forming a border around the envelope.

Where the backing layer forms a border around the envelope, the border may carry an adhesive that may serve to adhere the wound dressing to the patient's skin around the wound. The size of the dressing will generally be chosen such that the envelope overlies the wound and the border contacts healthy skin around the wound. Suitable skin contact adhesives for wound dressings are known, and any suitable adhesive known in the art may be used in the present invention. For example, the adhesive may be an acrylic adhesive, hydrocolloid adhesive, polyurethane adhesive, hydrogel or soft silicone adhesive.

Soft silicone adhesives offer numerous advantages. Most preferably, the soft silicone adhesive is in the form of a silicone gel.

Soft silicone adhesives are particularly suited for use as skin contact layers in wound dressings. They are soft, tactile and conformable, and exhibit good adhesion to dry skin but low adherence to an underlying wound. Thus, the dressing can be applied to a wound and subsequently removed without causing trauma to the wound. Silicone gels are adhesive but do not leave fibres or residue on a surface/substrate when removed.

Silicone gels suitable for use as skin contact materials in the present invention may be carried on a layer of melt-blown non-woven material, eg a sheet of melt-blown polyurethane (MBPU), as described in WO2007/113597. The reverse side of the MBPU may be coated with an adhesive, eg an acrylic adhesive, to affix the silicone gel/MBPU laminate to the overlying components of the dressing, eg the backing layer.

The adhesive may be provided only at the border of the dressing, ie on the underside of the backing layer that extends beyond the envelope. Alternatively, however, the adhesive may extend across the entire extent of the underside of the wound dressing, covering the wound-facing surface of the envelope. In such a case, the adhesive layer will generally be provided with openings, eg relatively large perforations, to allow the transfer of wound exudate through the adhesive layer and into contact with the wound-facing surface of the envelope. In such cases, the adhesive layer overlies and contacts the wound itself, rather than just the surrounding healthy skin, and so it is generally preferable that the adhesive that is used is one that is non-adherent and permits the wound dressing to be removed relatively easily and without causing trauma to the wound. Thus, the adhesive may be, for instance, a hydrocolloid adhesive, a polyurethane adhesive, a hydrogel or, most preferably, a soft silicone adhesive, particularly a silicone gel. The silicone gel may be carried on a sheet of MBPU, in which case the MBPU/silicone laminate may be formed with a regular array of relatively large perforations, eg perforations having a diameter of 2-10 mm or more, eg 4-10 mm. Perforations may also be provided in an adhesive layer which is present only at the border of the dressing. In such a case, the perforations may be relatively small, and are provided to increase breathability of the dressing.

Where the wound dressing includes a skin contact adhesive, the dressing will generally be supplied with a releasable liner on its underside. The releasable liner may cover the adhesive and wound contact portions of the wound dressing prior to use, and be removed from the dressing immediately before application of the dressing to the wound. This reduces the risk of contamination of the wound dressing and facilitates handling of the dressing.

Such releasable liners are commonly used on wound dressings known in the art, and suitable materials which can be employed in the present invention will be familiar to the skilled worker. For example, the releasable liner may be of a suitable plastics sheet or a siliconised paper or the like.

The releasable liner may be a single sheet which covers the underside of the wound dressing, or may be formed of two or more sheets. The releasable liner may further comprise a tab to enable the liner to be easily removed from the dressing before use. In particular, where the releasable liner is formed of two or more parts, the parts may either overlap or abut and extend outwards from the wound dressing, thus providing an easy method for removal of the releasable liner.

The invention will now be described in greater detail, by way of example only, with reference to the accompanying drawings.

Figure 2:
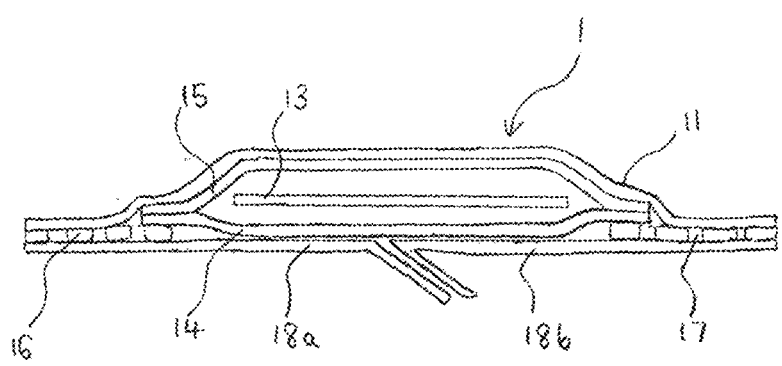
FIG. 2 is a cross-sectional view, not to scale, on the line II-II in FIG. 1.

In FIGS. 1 and 2, there is shown a first embodiment of a wound dressing according to the invention, generally designated 1. The dressing 1 is generally square in form and comprises a backing layer 11 of microporous polyurethane film, to a central portion of which is affixed an envelope containing a sheet of superabsorbent material 13.

The envelope comprises a wound-facing square sheet of gelling material 14 knitted from a blended alginate/Tencel yarn material and a sheet of dry web polyester material 15, the outer surface of which is bonded to the backing layer 11 by means of acrylic adhesive. The gelling material 14 and the dry web polyester material 15 are thermally bonded to each other at their edges. The sheet of superabsorbent material 13 comprises particles of sodium polyacrylate polymer encapsulated between two layers of tissue paper carrier material. The sheet of superabsorbent material 13 is slightly smaller than the internal dimensions of the envelope such that it fits inside.

A silicone gel skin contact layer 16 is present around the border of the dressing and partially overlaps the gelling material 14. In other words, the silicone gel layer 16 is formed with a central opening that is slightly smaller in size than the gelling material 14, so that the majority of the gelling material 14 is exposed and, in use, directly contacts the wound. In FIG. 1, the edges of the gelling material 14 (ie of the envelope containing the superabsorbent material 14) are shown in broken lines.

The silicone gel skin contact layer 16 comprises a sheet of melt-blown polyurethane that carries a coating of silicone gel. The reverse side of the melt-blown polyurethane is coated with acrylic adhesive by which it is affixed to the border of the backing layer 11 and to the edge regions of the gelling material 14. The silicone gel layer 16 is formed with a regular array of small perforations 17 that result in the layer being breathable. In use, the silicone gel layer 16 contacts the skin around the edge of the wound, and the knitted gelling material 14 contacts the wound directly.

The wound dressing 1 is supplied with a two-part release liner 18a,18b, which is removed from the dressing 1 immediately prior to use, in order to expose the knitted gelling material 14 and the surrounding silicone gel layer 16.

When the dressing 1 is applied to a wound, the open knitted structure of the gelling material 14 allows wound exudate to pass through it into the interior of the envelope where it is absorbed by the superabsorbent material 13. At the same time, the knitted gelling material 14 itself absorbs wound exudate and is converted to a non-adherent gel. Thus, the gelling material 14 serves to retain the superabsorbent material 13 yet permits wound exudate to pass through it, so as to be absorbed by the superabsorbent material 13, whilst also presenting a non-adherent surface to the wound.

The dressing 1 may be manufactured by the following general method.

First, a pre-laminate comprising the silicone gel layer is produced in the manner described in WO2007/113597. In general terms, this involves applying silicone gel precursors to a sheet of melt-blown polyurethane (MBPU), the underside of which carries a coating of acrylic adhesive and a temporary protective backing, eg of plastics film or paper. Once the silicone gel precursors have cured, to produce a hydrophobic silicone gel, a temporary cover, again of plastics film or paper material, is applied to the gel. Perforations and square openings corresponding to the perforations 17 and central opening of the finished dressing 1 are then formed in the pre-laminate.

In a separate operation, envelopes containing sheets of superabsorbent material are produced by sandwiching appropriately sized pieces of such material between layers of knitted gelling material and dry web polyester, and fusing the knitted gelling material and polyester together by means of heated platens around the edges of the superabsorbent material. Individual envelopes are then cut out.

The individual envelopes are then positioned on a sheet of breathable polyurethane film (which constitutes the backing layer 11 of the finished dressing 1). The temporary protective backing is removed from the underside of the MBPU to expose the acrylic adhesive and the pre-laminate is applied to the polyurethane film with the square openings in registration with the envelopes, such that the acrylic adhesive bonds to the polyurethane film and to the edges of the envelopes. Finally, the temporary protective cover is removed from the silicone gel and replaced with appropriately formed release liners, and individual dressings 1 are punched out and sterile-packaged.

Figure 3:
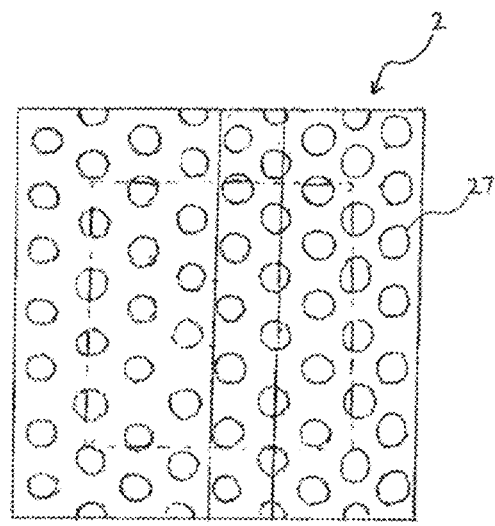
FIG. 3 is a view similar to FIG. 1 of a second embodiment of a wound dressing according to the invention, with a silicone gel skin contact layer that extends across the full extent of the underside of the dressing.

A second embodiment of a wound dressing, generally designated 2, is shown in FIG. 3. This dressing 2 is broadly similar to the dressing 1 of FIG. 1.

In the dressing of FIG. 3, however, the silicone gel skin contact layer extends across the whole extent of the underside of the dressing. The silicone gel layer is not formed with a central opening akin to that present in the dressing 1 of FIGS. 1 and 2, but instead has a regular array of perforations 27 that are much larger than the perforations 17 of the dressing 1. The perforations 27 have approximate diameter 5 mm, to permit wound exudate to pass from the wound into the knitted gelling material and the superabsorbent material. In the case of the dressing 2, therefore the silicone gel layer contacts not only the healthy skin around the wound, but also the wound itself, with the gelling material exposed to the wound through the large perforations 27. This dressing 2 therefore relies upon the non-adherent properties not only of the gelling material but also of the silicone gel skin contact layer to permit the dressing 2 to be removed from the wound without trauma or pain.

Figure 4:
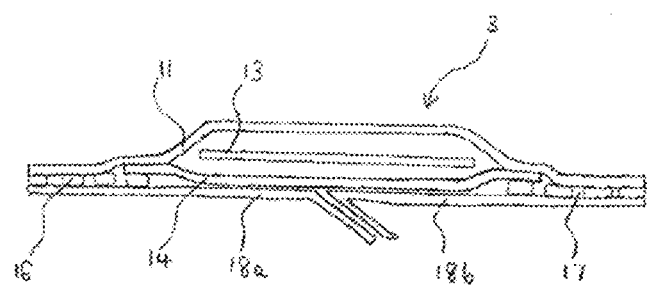
FIG. 4 is a cross-sectional view of a third embodiment of a wound dressing, which differs from the first embodiment of FIGS. 1 and 2 by the reverse sheet of the envelope being formed by the backing layer.

In FIG. 4 there is shown a third embodiment of a wound dressing according to the invention, generally designated 3. Features shared with the first embodiment are designated by the same reference numbers, and only differences between the first and third embodiments are described with reference to the third embodiment of FIG. 4. In this embodiment, the reverse sheet of the envelope is the backing layer 11, ie the superabsorbent material 13 is contained within an envelope constructed from a sheet of fabric knitted or woven from yarn comprising gelling fibres 14 that is affixed to a backing layer 11. As shown, the backing layer 11 is of greater dimensions than the sheet of knitted or woven fabric 14, such that the backing layer extends beyond the knitted or woven fabric sheet and provides a means of affixing the wound dressing to the skin via silicone gel layer 16.

The invention claimed is:

1. An absorbent wound dressing comprising a superabsorbent material that, in use, is adapted to be in fluid communication with the surface of a wound upon which the absorbent wound dressing is applied, wherein the superabsorbent material is enclosed in an envelope having a non-wound-facing surface and a wound-facing surface, wherein the wound-facing surface is knitted from a yarn comprising a blend of gelling fibres and non-gelling fibres, and wherein the superabsorbent material is sodium polyacrylate polymer.

2. The absorbent wound dressing according to claim 1, wherein the envelope is assembled from two sheets of material, with the superabsorbent material between said two sheets of material.

3. The absorbent wound dressing according to claim 2, wherein the non wound-facing surface is a polyester film or web.

4. The absorbent wound dressing according to claim 1, wherein the non-wound-facing surface of the envelope is exposed when the absorbent wound dressing is in use.

5. The absorbent wound dressing according to claim 1, wherein the envelope is formed by welding.

6. The absorbent wound dressing according to claim 5, wherein the welding is heat welding.

7. The absorbent wound dressing according to claim 1, wherein the superabsorbent material is in the form of particles.

8. The absorbent wound dressing according to claim 7, wherein the superabsorbent material particles are encapsulated between two layers of a carrier material.

9. The absorbent wound dressing according to claim 1, wherein the gelling fibre has an absorbency of at least 2 g/g.

10. The absorbent wound dressing according to claim 9, wherein the absorbency is at least 5 g/g, at least 10 g/g, at least 15 g/g, or at least 25 g/g.

11. The absorbent wound dressing according to claim 1, wherein the gelling fibres are pectin fibres, alginate fibres, fibres made from alginate and another polysaccharide, chitosan fibres, hyaluronic acid fibres, fibres of other polysaccharides or derived from gums, chemically-modified cellulosic fibres or a combination or blend of these fibres.

12. The absorbent wound dressing according to claim 11, wherein the gelling fibres are alginate fibres or pectin fibres.

13. The absorbent wound dressing according to claim 1, wherein the yarn comprises at least 50% w/w gelling fibres.

14. The absorbent wound dressing according to claim 1, wherein the non-gelling fibres are lyocell fibres.

15. The absorbent wound dressing according to claim 1, wherein the absorbent wound dressing comprises a backing layer that has a moisture vapour transmission rate of at least 300 g/m$^2$/24 h at 37° C.

16. The absorbent wound dressing according to claim 15, wherein the backing layer is a polyurethane film.

17. The absorbent wound dressing according to claim 15, wherein the backing layer is larger in size than the envelope.

18. The absorbent wound dressing according to claim 17, wherein the backing layer forms a border around the envelope.

19. The absorbent wound dressing according to claim 1, wherein at least part of the surface of the absorbent wound dressing that, in use, contacts a patient's skin is provided with a skin contact adhesive.

20. The absorbent wound dressing according to claim 19, wherein the skin contact adhesive is a soft silicone adhesive.

21. The absorbent wound dressing according to claim 19, wherein the skin contact adhesive is provided only at a border of the wound-facing surface.

22. The absorbent wound dressing according to claim 19, wherein the skin contact adhesive is provided in the form of a discontinuous pattern across the entire wound-facing surface of the absorbent wound dressing.

* * * * *